United States Patent [19]

Savins

[11] 4,078,332
[45] Mar. 14, 1978

[54] METHOD AND APPARATUS FOR THE SYNTHESIS OF ALGA BIOPOLYMER

[75] Inventor: Joseph George Savins, Dallas, Tex.

[73] Assignee: Mobil Oil Corporation, New York, N.Y.

[21] Appl. No.: 749,508

[22] Filed: Dec. 10, 1976

[51] Int. Cl.$^2$ .......................... A01G 7/00; C09K 3/00
[52] U.S. Cl. .................................. 47/1.4; 252/8.55 R
[58] Field of Search ...................... 47/1.4, 58; 252/8.55

[56] References Cited

U.S. PATENT DOCUMENTS

| | | | |
|---|---|---|---|
| 3,195,271 | 7/1965 | Golveke et al. | 47/1.4 |
| 3,879,890 | 4/1975 | Chen et al. | 47/1.4 |
| 3,889,418 | 6/1975 | Porter et al. | 47/58 |
| 3,958,364 | 5/1976 | Schenck et al. | 47/1.4 |
| 3,969,844 | 7/1976 | Fogel et al. | 47/58 |

OTHER PUBLICATIONS

The Production of —, Ramus, Jnl. of Phycol., 8, 1972, pp. 97-111.

*Primary Examiner*—Robert E. Bagwill
*Attorney, Agent, or Firm*—C. A. Huggett; William D. Jackson

[57] ABSTRACT

This specification discloses a method and apparatus for the synthesis of alga biopolymer. The method is comprised of two stages and involves subjecting an aqueous culture containing alga cells and nutrients required for the growth of the alga cells to a first stage of artificial illumination for a period of time such that growth of the alga and synthesis of biopolymer begins followed by a second stage of natural illumination provided by successive cycles of diurnal solar radiation and darkness. During the cycles of diurnal solar radiation and darkness in the second stage, the aqueous culture is continuously contacted with a mixture of carbon dioxide and air. Furthermore, during these cycles of diurnal solar radiation and darkness, the temperature of the aqueous culture is maintained at a level conducive to the growth of the alga cells. The apparatus is employed in the second stage and contains a lower chamber adapted to contain an aqueous thickening culture from a stage-one reactor. Means are provided for passing continually into the chamber and into contact with the aqueous culture a mixture of carbon dioxide and air. Means are also provided for maintaining the temperature of the aqueous culture at a level conducive to growth of the alga cells. There is also provided an upper chamber enclosed at the top portion thereof with a hemispherical radiant energy receiver capable of receiving incident solar radiation and being substantially transparent to the solar radiation. Conduit means are provided to transfer the aqueous culture from the lower chamber to the upper chamber. Means for impinging the aqueous culture upon the underside of the hemispherical radiant energy receiver are also provided. There are also provided means for returning the aqueous culture to the lower chamber from the upper chamber after impinging upon the underside of the hemispherical radiant energy receiver.

12 Claims, 7 Drawing Figures

METHOD AND APPARATUS FOR THE SYNTHESIS OF ALGA BIOPOLYMER

BACKGROUND OF THE INVENTION

1. Field of the Invention

The invention relates to a method and apparatus for the synthesis of alga biopolymer.

2. Description of the Prior Art

Methods for the growth of alga and synthesis of alga constituents are known. For example, U.S. Pat. No. 3,195,271 discloses a method for the growth of the alga *Porphyridium cruentum*. This patent also discloses the synthesis of the alga constituent, carrageenin. Procedures for the growth of alga are disclosed in "Algal Culture: From Laboratory to Pilot Plant", J. S. Burlew, Ed., Carnegie Inst. of Washington, Publication No. 600, Washington, D.C. (1964), and "Properties and Products of Algae", J. E. Zajic, Ed., Plenum Press, New York (1970). It is also known that many marine and fresh water species of alga liberate synthesis products into their surroundings, Hoyt, J. W. and Soli, G., *Science*, 149, 1509 (1965). A culture for the growth of the alga *Porphyridium aerugineum*, known as the MCYII medium, is disclosed by Ramus, J. in the *Jnl. Phycol.*, 8 [1], 97 (1972) and by Gantt, E. et al., in the Jnl. Phycol., 4 (65) 1968.

SUMMARY OF THE INVENTION

The invention encompasses a method and apparatus for the synthesis of alga biopolymer. The alga biopolymer is synthesized by a two-stage method wherein an aqueous culture containing alga cells and nutrients required for the growth of the alga cells is subjected to a first stage of artificial illumination followed by a second stage consisting of successive cycles of diurnal solar radiation and darkness. In the first stage, three radiant energy related parameters of the artificial illumination are manipulated. These parameters are: (1) $\psi_a$, an "intrinsic slope" or the initial linear gradient of the cumulative absorbed radiant energy versus time curve evaluated over the initial period of $0 < t < 2$ days; (2) $(E_a)_c$, the cumulative moles of radiant energy quanta absorbed by the illuminated culture during the first stage; and (3) $\theta_l$, the lag time preceding the phase of rapid synthesis of biopolymer. Further, in the first stage, the energy content of the artificial illumination may be enriched with respect to particular wavelengths. The aqueous culture is continuously contacted with a mixture of carbon dioxide and air during the second stage of successive cycles of diurnal solar radiation and darkness. Moreover, the temperature of the aqueous culture in the second stage is maintained at a level conducive to the growth of the alga cells during the cycles of diurnal solar radiation and darkness. The method of the second stage can be carried out in an apparatus containing a lower chamber adapted to contain the aqueous culture of alga cells. The apparatus includes means passing thereto aqueous culture from the first stage and means for passing continually into the chamber and into contact with the aqueous culture a mixture of carbon dioxide and air. The apparatus also includes means for maintaining the temperature of the aqueous culture at a level conducive to the growth of the alga cells. The apparatus also includes an upper chamber enclosed at the top portion thereof with a hemispherical radiant energy receiver capable of receiving incident solar radiation and being substantially transparent to the solar radiation. Conduit means are included to transfer the aqueous culture from the lower chamber to the upper chamber as well as means for impinging the aqueous culture upon the underside of the hemispherical radiant energy receiver. Means are also provided for returning the aqueous culture to the lower chamber after impinging upon the underside of the hemispherical radiant energy receiver.

DESCRIPTION OF THE PREFERRED EMBODIMENTS

Many algae, during their life cycle in a culture, synthesize extracellular biopolymers, and these extracellular biopolymers enter into solution in the culture. These biopolymers may be of a viscous nature, thus imparting thickening to an aqueous medium containing them. Various uses for these biopolymers are known to the art. Recently they have been proposed as a thickening agent for aqueous driving fluids employed for the recovery of petroleum from a subterranean petroleum-containing formation.

The present invention is directed to a method and apparatus for the growth of alga and the concomitant synthesis of biopolymer. The biopolymer may be employed as a thickening agent in aqueous driving fluids for the recovery of petroleum for a subterranean petroleum-containing formation. However, the biopolymer may also be employed otherwise as is known to the art.

The method and apparatus of the invention may be employed for the growth of, and synthesis of biopolymer from, various algae. Such algae may be from the divisions Chlorophyta, Phaeophyta, Rhodophyta, and Cyanophyta. In the division Chlorophyta, they may be from the genus Ulva. In the division Phaeophyta, they may be from the genera Ilea and Pelvetiopsis. In the division Rhodophyta, they may be from the genera Porphyra, Corallina, Gratelupia, Gymnogongrus, Stenogramma, and Rhodomenia. In the division Cyanophyta, they may be from the genus Anabaena. In the genus Porphyra, they may be the species *Porphyridium aerugineum* or *Porphyridium cruentum*. In the genus Anabaena, they may be the species *Anabaena flos-aquae*. In the division Chlorophyta, they may be the species *Chlorella stigmataphora*. Preferably, the method and apparatus of the invention is employed for the synthesis of biopolymer from the species *Porphyridium aerugineum*.

Algae, including *Porphyridium aerugineum*, as is known, require for their growth water, illumination, a carbon source, and certain other nutrients and nutrient-related materials. The illumination may be sunlight, i.e., solar radiation (natural illumination), or may be artificial illumination, or may be a combination of artificial and natural illumination. In the second stage of the method and in the apparatus of the invention, solar radiation is employed as the source of illumination. With algae which are obligate photoautotrophs, such as *Porphyridium aerugineum*, the source of carbon is customarily gaseous carbon dioxide. The gaseous carbon dioxide is normally supplied in admixture with air. The nutrients and nutrient-related materials are exemplified by the components, in addition to water, contained in the MCYII medium previously mentioned. This medium contains the distribution of macro and micro levels of inorganic ions, chelating agents, buffering agent, etc. set forth in Table I.

TABLE I

| MCYII Medium | | |
|---|---|---|
| Component | Amount | |
| NaNO$_3$ | 442 | mg |
| KCl | 30 | mg |
| CaCl$_2$ . 2H$_2$O | 36.6 | mg |
| FeCl$_3$ . 6H$_2$O | 1.9 | mg |
| MgSO$_4$ . 7H$_2$O | 100 | mg |
| Na$_2$ . glycerophosphate . 5H$_2$O | 90 | mg |
| Tricine buffer | 986 | mg |
| PII trace metal mix | 10 | ml |
| Vitamin B$_{12}$ | 3.5 | µg |
| Distilled water to | 1000 | ml |
| Adjust pH to 7.6 with NaOH | | |
| PII Metal Mix: | | |
| H$_3$BO$_3$ | 114.0 | mg |
| MnCl$_2$ . 4H$_2$O | 14.4 | mg |
| ZnSO$_4$ | 2.2 | mg |
| CoCl$_2$ . 6H$_2$O | 0.44 | mg |
| FeCl$_3$ . 6H$_2$O | 4.8 | mg |
| Na$_2$EDTA* | 100 | mg |
| Distilled water to | 100 | ml |

*Disodium salt of ethylene diamine tetraacetic acid

Other nutrients and nutrient-related materials are exemplified by the components, in addition to water, contained in another medium identified as the "Modified MCYII Medium". These components are set forth in Table II below.

TABLE II

| Modified MCYII Medium | | |
|---|---|---|
| Component | Amount | |
| MgSO$_4$ . 7H$_2$O | 100 | mg |
| NaNO$_3$ or | 442 | mg |
| Urea | 155 | mg |
| CaCl$_2$ | 28 | mg |
| FeCl$_3$ or | 1.43 | mg |
| C$_{10}$H$_{12}$FeN$_2$NaO$_8$ | 5.36 | mg |
| K$_2$HPO$_4$ or | 51 | mg |
| Na$_2$HPO$_4$ | 42 | mg |
| H$_3$BO$_3$ | 11.4 | mg |
| FeSO$_4$ . 7H$_2$O | 2.2 | mg |
| ZnSO$_4$ . 7H$_2$O | 1.44 | mg |
| KCl | 30 | mg |
| B$_{12}$ | 3.5 × 10$^{-6}$ | mg |
| CoCl$_2$ . 6H$_2$O | 0.044 | mg |
| (Na)$_2$EDTA | 10 | mg |
| Distilled water to | 1000 | ml |

The MCYII medium, the Modified MCYII medium, or other suitable medium, may be employed in the method of the invention.

In carrying out the method of the invention, an aqueous culture containing an inoculum of alga cells and containing nutrients required for the growth of the alga cells is subjected to a two-stage process. In the first stage, the culture containing the alga is subjected continuously to artificial illumination. In this stage, three radiant energy-related parameters of the artificial illumination are manipulated. These parameters are: (1) $\psi_a$, an "intrinsic slope" or the initial linear gradient of the cumulative absorbed radiant energy versus time curve evaluated over the initial period of $0 < t < 2$ days; (2) $(E_a)_c$, the cumulative moles of radiant energy quanta absorbed by the illuminated culture during the first stage; and (3) $\theta_l$, the lag time preceding the phase of rapid synthesis of biopolymer. In the synthesis of biopolymer from the alga *Porphyridium aerugineum*, the first stage of the process is carried out employing continuous artificial illumination of such intensity that $\psi_a$ is about 0.33 Einstein (0.0165 kw-hr) per day per liter of culture and for such time that $(E_a)_c$ is between about 0.66 to 0.89 Einstein (0.033 to 0.045 kw-hr) per liter of culture. With these values of $\psi_a$ and $(E_a)_c$, the value of $\theta_l$ can be expected to be about 40 hours. Further, in the first stage, the energy content of the artificial illumination may be enriched with respect to particular wavelengths. In the synthesis of biopolymer of by *Porphyridium aerugineum*, the illumination employed may have its energy content predominantly in the region of about 600 to 700 nanometers. By "predominantly" is meant that at least 50% of the energy in the illumination is in the region of 600 to 700 nanometers.

The first stage is continued during the lag time, i.e., for a period of time that sufficient radiant energy has been absorbed by the aqueous culture that rapid synthesis of the biopolymer begins. In the second stage, the artificial illumination of the culture is discontinued and the culture is subjected to diurnal cycles of solar radiation and darkness. Thus, during each 24 hours the aqueous culture undergoes a cycle wherein it is exposed to solar radiation during the time of the day when there is daylight and is in darkness during the time of the day when there is no daylight. In each diurnal cycle, the duration of each period of solar radiation and period of darkness will, of course, depend upon the time of the year and the latitude at which the method is carried out. The second stage is continued to completion of the biopolymer synthesis reaction, i.e., until the desired concentration of biopolymer or desired viscosity level in the aqueous culture is attained.

In accordance with the method of the invention, in the second stage the aqueous culture is continuously contacted with a mixture of carbon dioxide and air during the diurnal cycles of solar radiation and darkness. Whereas continued growth of the alga and synthesis of biopolymer occur only when the aqueous culture is simultaneously subjected to the solar radiation and contacted with the mixture of carbon dioxide and air, it would appear that continuous contact with the mixture of carbon dioxide and air during the period of darkness would be of no avail. Surprisingly, however, I have found that continuous contact with the mixture of carbon dioxide and air during both periods of illumination and darkness maintains a substantially uniform pH level in the aqueous culture with resulting improvement in the rate of synthesis of biopolymer.

In accordance with a feature of the method of the invention, the temperature of the aqueous culture during the diurnal cycles of solar radiation and darkness is maintained at a temperature conducive to growth of the alga cells. By a "temperature conducive to the growth of the alga cells" is meant a temperature at which the rate of growth of the alga cells is at a maximum commensurate with a minimum rate of growth of competing alga cells which may have accidentally or unavoidably contaminated the culture. With the alga *Porphyridium aerugineum*, the temperature of the culture is maintained between about 70° F. and 77° F. (21.1° and 25.0° C.). At temperatures above 77° F. (25.0° C.), species of green and blue algae compete with the red alga, *Porphyridium aerugineum*, for the available nutrients in the culture.

The proportion of carbon dioxide in the mixture of carbon dioxide and air may be between about 1 and 10 volume percent. Preferably, however, the proportion of carbon dioxide in the mixture is about 5 volume percent.

The following examples will further illustrate certain aspects of the invention.

EXAMPLE 1

This example will illustrate the fluctuations in pH of an aqueous culture of alga during diurnal cycles of illumination and darkness with contact of a mixture of carbon dioxide and air exclusively during the period of illumination.

*Porphyridium aerugineum* was grown and biopolymer synthesized in an aqueous culture containing the nutrients, with the exception of the tricine buffering agent, set forth in Table I above. The particular *Porphyridium aerugineum* that was employed is cataloged as isolate No. 755 in the alga culture collection maintained at Indiana State University, Bloomington, Indiana, e.g. see Starr, R. C., *Amer. Jnl. Bot.*, 51 [9], 1013 (1964). The alga was grown and the biopolymer synthesized at an average temperature of 77° F. (25° C.). Agitation was provided by the standard shake flask culture method. The aqueous culture was subjected to artificial illumination during the period from 8:00 A.M. to 4:00 P.M. each day and was in darkness during the period from 4:00 P.M. until the following 8:00 A.M. During the period of illumination a mixture of 5% by volume of carbon dioxide entrained with 95% by volume of air was injected into the aqueous culture at a rate of 500 cubic centimeters per minute per liter. The injection of the mixture of carbon dioxide and air also provided a measure of agitation. During the periods of darkness, there was no injection of the mixture of carbon dioxide and air. The illumination during the 8:00 A.M. to 4:00 P.M. period of each diurnal cycle was undefined but was provided via ceiling-mounted and auxiliary fluorescent lights. Levels of illumination and radiant energy incident to the aqueous culture were on the order of 800 foot-candles (8061.12 lux) and $10^4$ ergs/cm$^2$ sec ($10^3$ microjoules/cm$^2$ sec). The pH of the culture was measured at daily intervals at the end of each period of illumination and of darkness.

Figure 1:
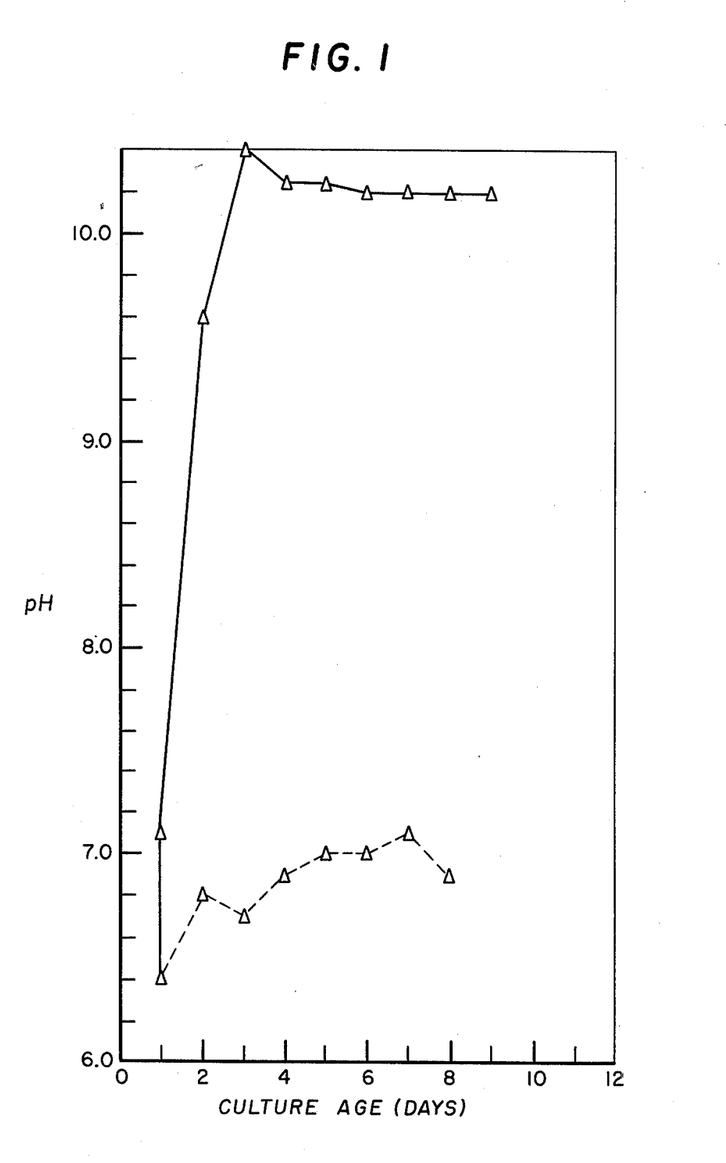
FIG. 1 is a plot of pH versus age for an aqueous culture containing alga cells and nutrients for the growth of the alga cells, the culture being subjected to successive cycles of diurnal artificial illumination and darkness and being contacted with a mixture of carbon dioxide and air only during the period of radiation.

The results are given in FIG. 1. In FIG. 1, the dotted line indicates the pH at the end of the period of illumination during which period the mixture of carbon dioxide and air had been injected into the culture and the continuous line indicates the pH at the end of the period of darkness during which period there had been no injection of the mixture of carbon dioxide and air.

It will be seen from FIG. 1 that there were wide fluctuations in the pH of the aqueous culture depending upon whether the mixture of carbon dioxide and air was injected into the aqueous culture. For example, during the first day, the pH at 8:00 A.M. was 7.1 but at 4:00 P.M. was 6.4. On the second day, the pH at 8:00 A.M. was 9.6 but at 4:00 P.M. was 7.8. The pH on the third day at 8:00 A.M. was 10.4 but at 4:00 P.M. was 6.7. Thereafter, the pH at 8:00 A.M. remained at about 10.2 and at 4:00 P.M. varied between 6.9 and 7.1.

EXAMPLE 2

This example will illustrate that fluctuations in pH of an aqueous culture of growing alga during diurnal cycles of illumination and darkness with contact of a mixture of carbon dioxide and air exclusively during the period of illumination occur even when the aqueous culture contains a pH buffering agent.

The procedure of Example 1 was repeated with the exception that the aqueous culture contained all of the components of the MCYII medium set forth in Table I including the 986 mg per 1000 ml of aqueous culture of the tricine pH buffering agent.

Figure 2:
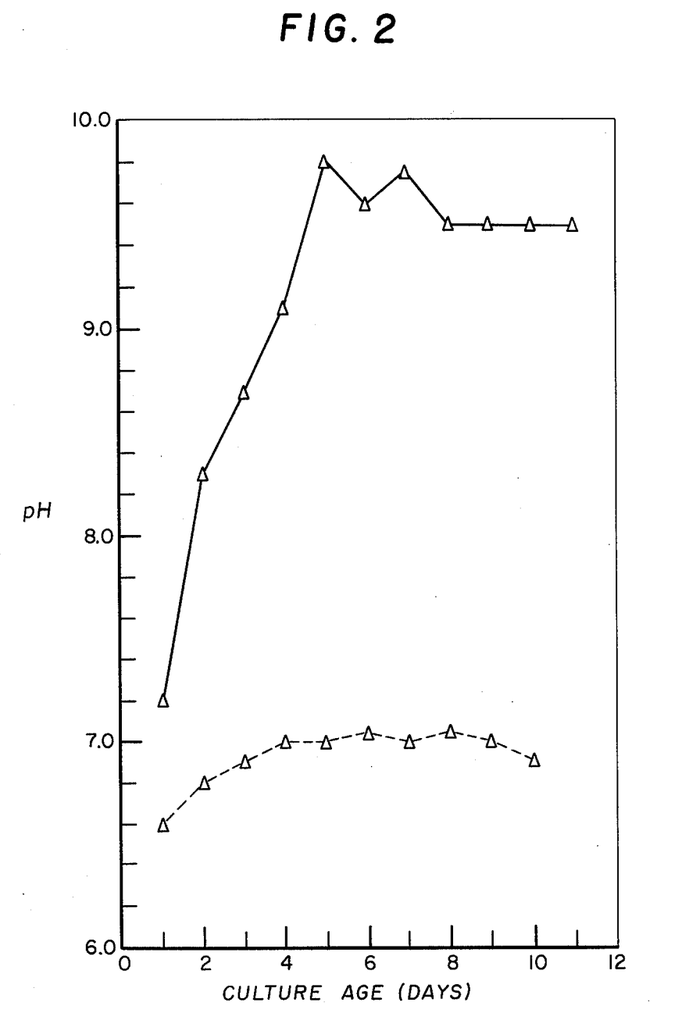
FIG. 2 is a similar plot with the exception that the aqueous culture contained a pH buffering agent.

The results are given in FIG. 2. It will be observed from the Figure that on the first day, the pH at 8:00 A.M. was 7.2 and at 4:00 P.M. was 6.6. On the second day, the pH at 8:00 A.M. was 8.3 and at 4:00 P.M. was 6.8. On the third day, the pH at 8:00 A.M. was 8.7 and at 4:00 P.M. was 6.9. From the fourth day on, the pH at 8:00 A.M. varied between 9.1 and 9.9 whereas at 4:00 P.M. the pH varied slightly at about 7.0. Thus, it will be seen that the presence of the tricine pH buffering agent in the aqueous culture had no significant effect on the fluctuations in pH of the aqueous culture with contact of the mixture of carbon dioxide and air exclusively during the period of illumination.

EXAMPLE 3

This example will illustrate the substantial uniformity of the pH of an aqueous culture of an alga during diurnal cycles of illumination and darkness with continuous contact of a mixture of carbon dioxide and air.

The procedures of Examples 1 and 2 were repeated with the exception that the mixture of carbon dioxide and air was injected into the aqueous cultures continuously during both the periods of illumination and of darkness.

Figure 3:
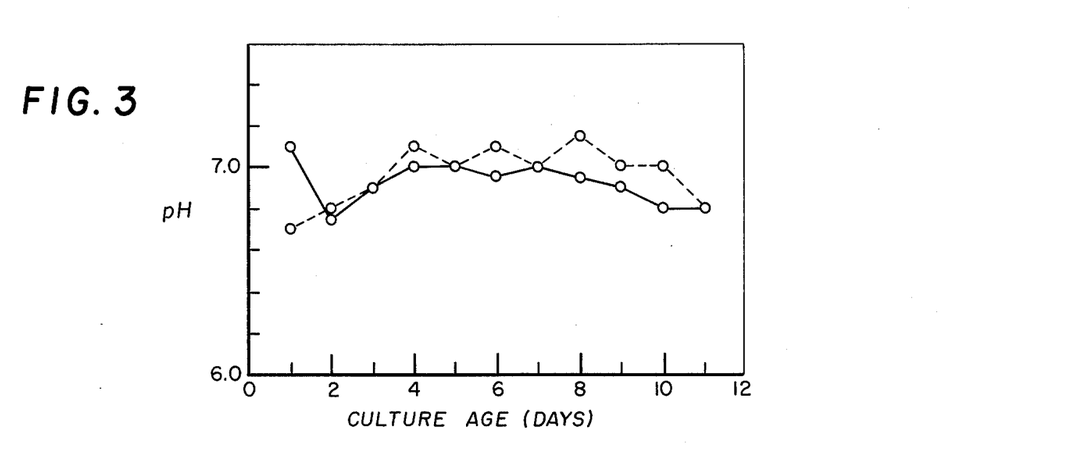
FIG. 3 is a plot similar to FIG. 1 with the exception that contact of the aqueous culture with the mixture of carbon dioxide and air was continuous during the successive cycles of diurnal artificial illumination and darkness.
Figure 4:
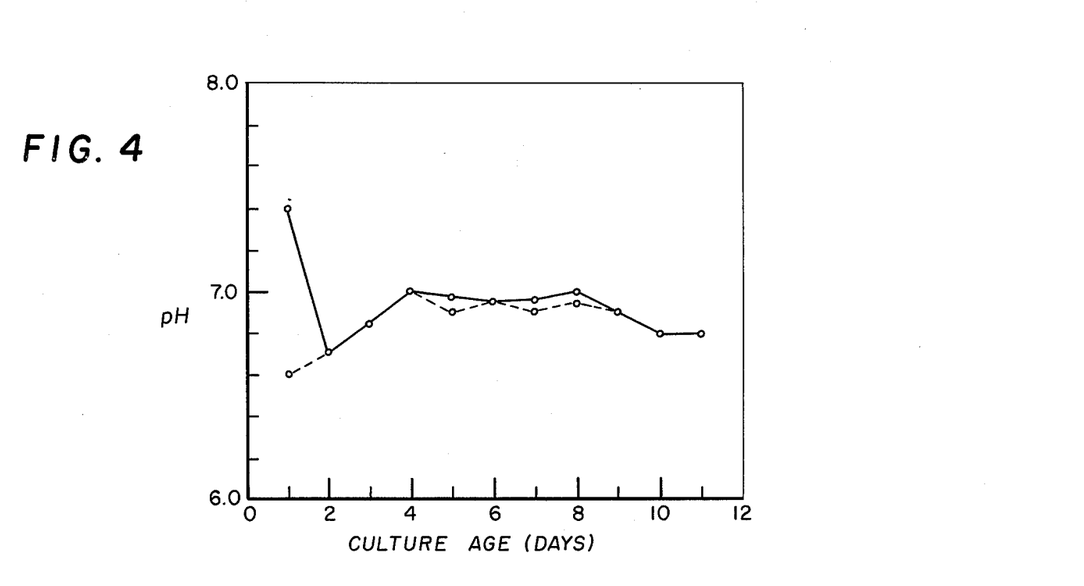
FIG. 4 is a plot similar to FIG. 1 with the exception that the aqueous culture contained a pH buffering agent.

The results are given in FIGS. 3 and 4. FIG. 3 gives the results for the procedure where the aqueous culture did not contain the tricine pH buffering agent. FIG. 4 gives the results for the procedure where the aqueous culture contained the tricine pH buffering agent.

It will be seen from FIGS. 3 and 4 that, with the exception of the first day, before equilibrium had been established, the pH of the aqueous cultures remained substantially at a level of about 7 for both the periods of illumination and of darkness.

EXAMPLE 4

This example will illustrate the improvement in the kinetics of biopolymer synthesis with continuous contact of the aqueous culture with the mixture of carbon dioxide and air during both the periods of illumination and of darkness of the diurnal cycle.

During the procedures of each of Examples 1-3, samples of the aqueous cultures were taken daily and their apparent viscosities determined. The apparent viscosities of the cultures are measures of the amount of biopolymer in the cultures, the higher the apparent viscosity the greater the amount of biopolymer. The apparent viscosities were measured at a shear rate of 1.7 $sec^{-1}$ employing a Brookfield viscometer fitted with a U.L. adapter.

Figure 5:
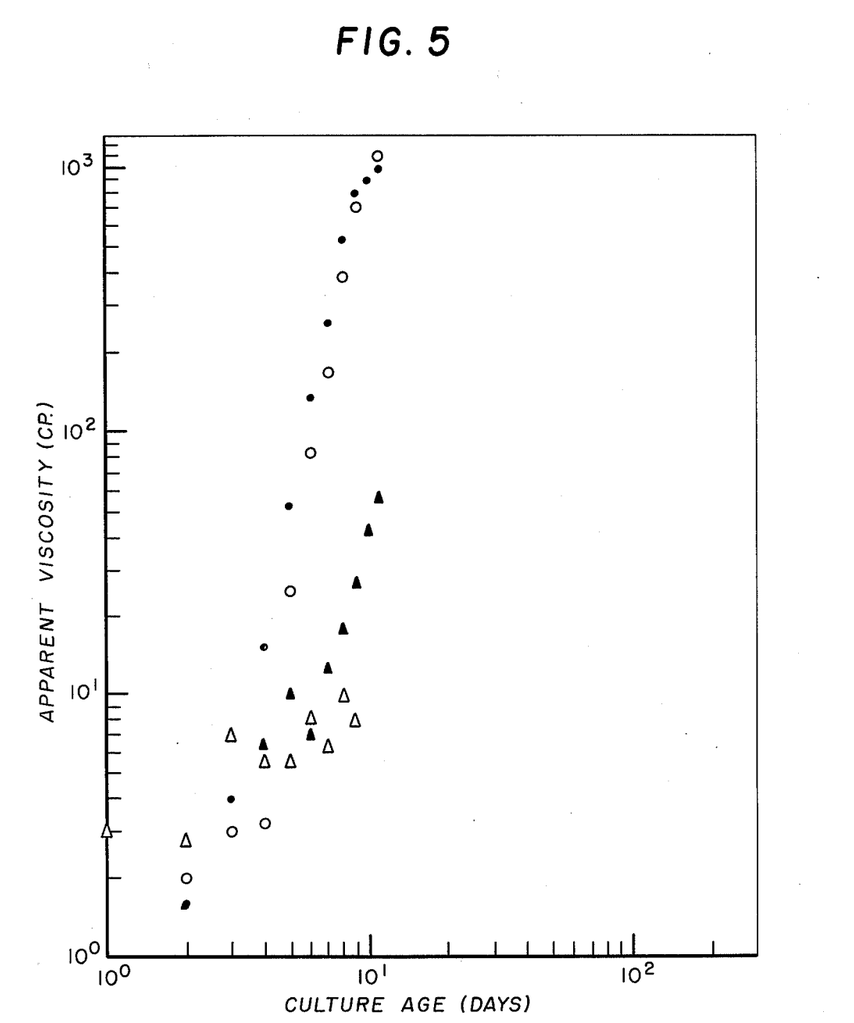
FIG. 5 is a plot of apparent viscosity versus age of four aqueous cultures containing alga cells and nutrients for the growth of the alga cells, the cultures being subjected to successive cycles of diurnal artificial radiation and darkness. Two of the cultures contained a pH buffering agent. Furthermore, two of the cultures were contacted with a mixture of carbon dioxide and air only during the period of artificial illumination and the remainder were contacted with the mixture of carbon dioxide and air continuously during the successive cycles of diurnal artificial illumination and darkness.

The results are given in FIG. 5. In the Figure, the triangles indicate the apparent viscosities attained with contact of the mixture of carbon dioxide and air exclusively during the periods of illumination, the solid and empty triangles being for the cultures containing and not containing, respectively, the tricine pH buffering agent. The circles indicate the apparent viscosities attained with contact of the mixture of carbon dioxide and air continuously during both the periods of illumination and of darkness of the diurnal cycle, the solid and empty circles being for the cultures containing and not containing, respectively, the tricine pH buffering agent.

It will be observed from FIG. 5 that, with continuous contact of the mixture of carbon dioxide and air during both the periods of illumination and darkness of the diurnal cycle, a greater amount of biopolymer is synthesized after the fourth day when pH equilibrium has been established than with contact of the mixture of carbon dioxide and air exclusively during the period of illumination of the diurnal cycle.

EXAMPLE 5

This example will illustrate the affect of culture temperature upon the kinetics of biopolymer synthesis.

In this example, a series of cultures of two species of Porphyridium alga were grown, and biopolymer thereby synthesized, at temperatures between 70° F. and 90° F. (21.1° C. and 32.2° C.). One of the alga species was *Porphyridium aerugineum* and was the same isolate employed in the previous examples. The other alga species was Porphyridium sp. and is cataloged as isolate No. 637 in the alga culture collection maintained at Indiana State University. The *Porphyridium aerugineum* was grown in a culture containing the nutrients set forth in Table I and the Porphyridium sp. was grown in a culture containing the nutrients set forth in Table II. The conditions of alga growth and biopolymer synthesis were as described in the previous examples. Alga growth and biopolymer synthesis were continued for 14 days. At the end of 8 days and 14 days, samples of each culture were taken and analyzed for the concentration of biopolymer.

Figure 6:
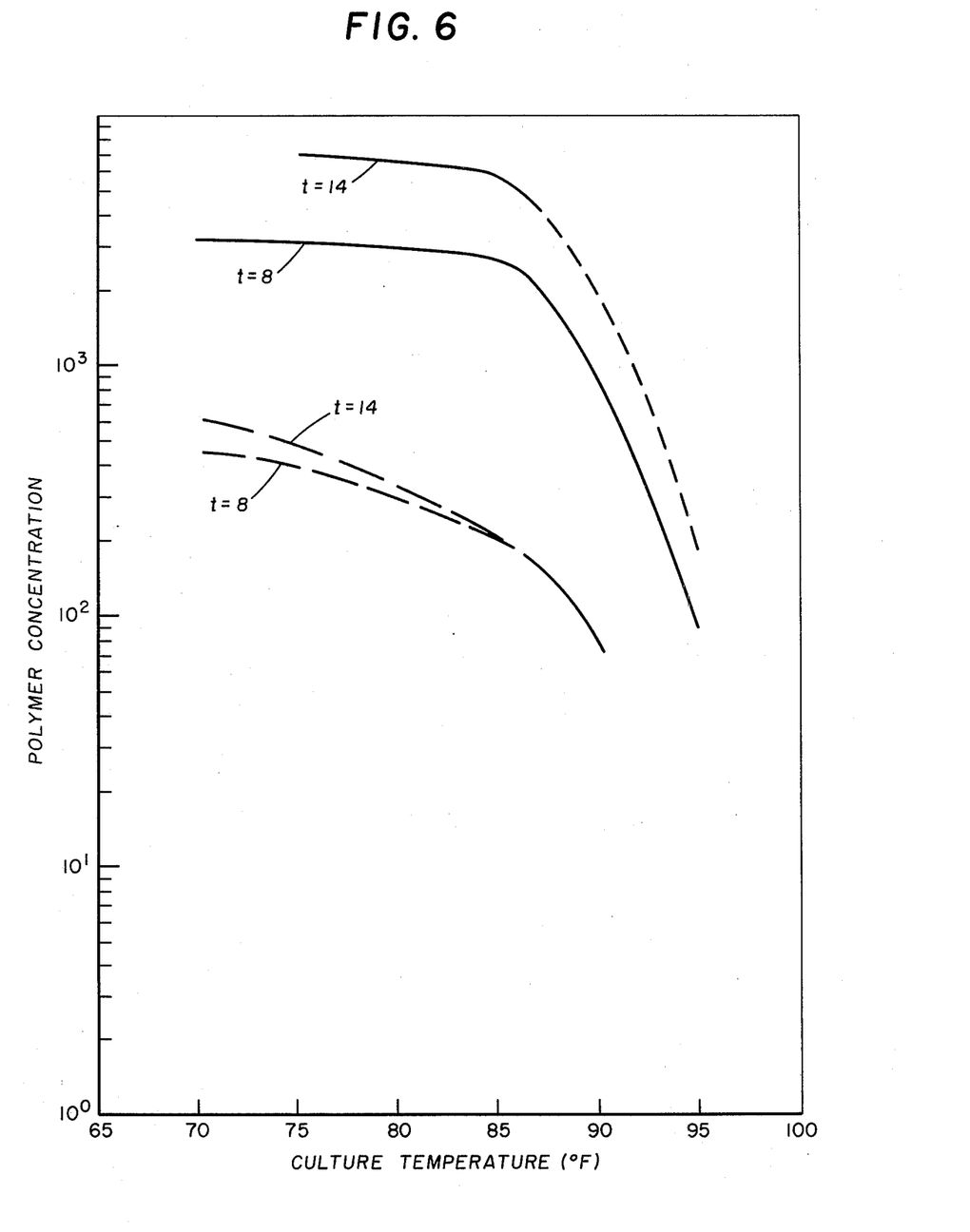
FIG. 6 is a plot of biopolymer concentration versus temperature at two different ages for two different species of alga grown in aqueous cultures containing nutrients for the growth of the alga.

The results are set forth in FIG. 6. In FIG. 6, the indicated parameter for each of the four curves is culture age in days. The dotted curves are for the Porphyridium sp. and the continuous curve is for the *Porphyridium aerugineum.* The biopolymer concentration is given in terms of weight parts per million of the aqueous culture.

It will be observed from the Figure that maximum biopolymer concentration was attained at the lower temperature range and the concentration decreased as the temperature of growth was increased. With the *Porphyridium aerugineum,* between the temperatures of 70° F. and 77° F. (21.1° C. and 25.0° C.), the biopolymer concentration attained remained substantially at a maximum but began to decrease with higher temperatures. With the Porphyridium sp., maximum biopolymer concentration was attained at 70° F. but decreased with higher temperatures.

Figure 7:
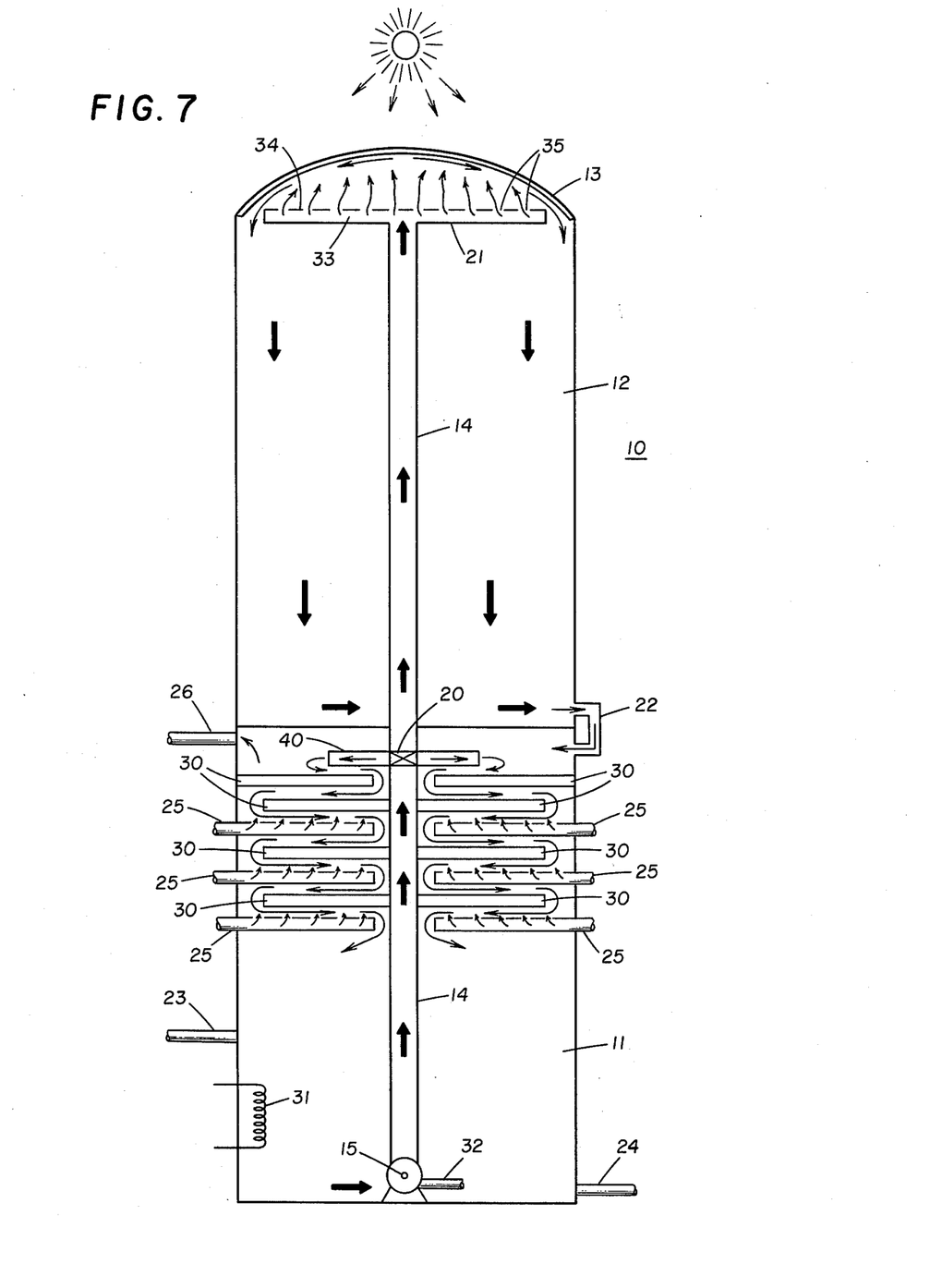
FIG. 7 is a schematic representation of an apparatus of the invention.

Reference will now be made to FIG. 7 for a description of an embodiment of the apparatus of the invention.

The apparatus 10 for the synthesis of biopolymer has a lower chamber 11 and an upper chamber 12. The upper chamber 12 is enclosed at the top portion thereof with a hemispherical radiant energy receiver 13. Conduit means 14 extends the length of the upper and lower chambers and is provided with pump 15 and valve 20. The conduit means 14 leads to a liquid impinging means 21 and a return line 22 connects the upper and lower chambers.

The lower chamber 11 is adapted to contain an aqueous culture of alga. It is provided with an inlet line 23 for an aqueous thickening culture of alga from a first-stage reactor and with an outlet line 24 for removal of the aqueous culture of alga containing biopolymer after growth of the alga and synthesis of the biopolymer has been completed. The lower chamber 11 also is provided with a plurality of inlets 25 and an outlet 26 for a mixture of carbon dioxide and air. These inlets are mounted horizontally within the lower chamber and extend inwardly from the wall of the chamber. The lower chamber 11 is also provided with a plurality of baffle plates 30. These baffle plates are also mounted horizontally within the lower chamber 11. They are supported by the conduit 14 and extend outwardly from the conduit toward the wall of the chamber. The baffle plates 30 and the inlets 25 for the mixture of carbon dioxide and air are positioned relative to each other such that each baffle plate has an inlet for the mixture of carbon dioxide and air below it. The lower chamber 11 is further provided with temperature controlling means 31 which may take the form of a coil or coils through which a heating or cooling medium may be circulated. The temperature controlling means is preferably located near the lower portion of the chamber 11. Pump 15 is provided with an inlet 32 within the lower chamber and its outlet is the conduit 14.

As mentioned, the conduit 14 leads to the liquid impinging means 21. The liquid impinging means is located near to and underneath the hemispherical radiant energy collector. The liquid impinging means may be of any suitable form. As illustrated, it may take the form of a liquid collecting tray 33 covered by a plate 34 provided with a plurality of perforations 35. The cover plate 34 may also comprise a porous plate or a surface otherwise comprised of a multitude of orifices, slots, or nozzles.

The hemispherical radiant energy collector 13 is capable of receiving incident solar radiation. Stated otherwise, the hemispherical radiant energy collector is exposed to the sky at least during periods of daylight. The collector is also substantially transparent to solar radiation. By "substantially transparent to solar radiation" is meant that the major portion, at least 50%, of those wavelengths of solar radiation required for the growth of alga will penetrate the collector. Thus, the hemispherical radiant energy collector is of such a thickness and is constructed of a material such that at least 50% of the solar radiation having wavelengths in the range from 200 to 700 nanometers, preferably in the range of 600 to 700 nanometers will pass through the cover. Illustrative of a suitable material of constriction of the cover is the clear plastic, polymethylmethacrylate, sold under the trade name "Plexiglas".

In operation, aqueous thickening culture from the first-stage reactor is introduced into the reactor through inlet line 23. Pump 15 is started and a mixture of carbon dioxide and air is introduced through the inlets 25. During daylight hours the valve 20 is open and the aqueous culture passes through the conduit 14 to the collecting tray 33 from which it passes through the perforations 35 and impinges upon the underside of the hemispherical radiant energy collector 13. As a result, the aqueous culture is distributed in the form of a finely divided spray or sheet against the inner surface of the hemispherical radiant energy collector. When delivered in this manner, the result is a thin film illumination effect with minimum attenuation of incident solar radiation. The aqueous culture drains from the underside of the hemispherical radiant energy collector and falls to the bottom of the upper chamber 12. The aqueous culture then passes through the line 22 to the bottom chamber 11. Upon entering the bottom chamber 11, the aqueous culture distributes itself over the baffle plates 30 in downward flow through the chamber and is contacted counter-currently with the upward rising mixture of carbon dioxide and air. The mixture of carbon dioxide and air is removed from the lower chamber through line 26 and may be recycled through the inlets 25 after replenishment of its carbon dioxide content. The aqueous culture after contact with the mixture of carbon dioxide and air collects at the bottom of the lower chamber 11 and is again pumped through the conduit 14 to impinge upon the underside of the hemispherical radiant energy collector 13. The cycle of pumping the aqueous culture after contact with a mixture of carbon dioxide and air through the conduit 14 to impinge upon the underside of the hemispherical radiant energy collector 13 is continued throughout the daylight hours.

With the cessation of daylight, and darkness having fallen, valve 20 is closed but the operation of pump 15 is continued during the period of darkness. During the period of darkness, the aqueous culture passes upward through the conduit 14 only as far as valve 20 and leaves the conduit through line 40. From line 40, the aqueous culture distributes itself over the baffles 30 and contacts in countercurrent flow the mixture of carbon dioxide and air. It will be seen when the valve 20 is open, the aqueous culture will impinge upon the underside of the hemispherical radiant energy collector and will not flow out of the line 40. When the valve 20 is closed, the opposite will occur.

With the next period of daylight, valve 20 is opened and the aqueous culture again impinges upon the underside of the hemispherical radiant energy collector 13 and thereafter passes into the lower chamber 11 to contact the mixture of carbon dioxide and air. With the next period of darkness, the valve 20 is closed and the aqueous culture no longer impinges upon the underside of the hemispherical radiant energy collector 13 but only circulates over the baffle plates 30 and contacts the mixture of carbon dioxide and air. The cycle of operating with the valve 20 open during periods of daylight and closed during periods of darkness is repeated diurnally until the desired concentration of biopolymer in the aqueous culture is attained.

When the final desired concentration of biopolymer in the aqueous culture is attained, the aqueous culture is removed from the lower chamber through outlet line 24 for such treatment or processing as is desired.

The temperature controller 31 is positioned in the lower portion of the lower chamber 11 to be immersed in the aqueous culture in the chamber 11. During daylight hours, the temperature controller may be employed to cool the aqueous culture to maintain the desired temperature if the aqueous culture has been heated by exposure to the solar radiation or by the ambient temperature to above the desired level. The temperature controller may be employed to heat the aqueous culture to the desired temperature during periods of darkness, or even of daylight, where the ambient temperature contributes to the temperature of the aqueous culture being below the desired level.

I claim:

1. A method for the synthesis of alga biopolymer comprising in a first stage contacting an aqueous culture containing alga cells and nutrients required for the growth of said alga cells with a mixture of carbon dioxide and air and subjecting said aqueous culture to the action of artificial illumination of such intensity and for such time that synthesis of alga biopolymer begins and in a second stage subjecting said aqueous culture to diurnal cycles of solar radiation and darkness and contacting said aqueous culture continuously during said diurnal cycles of solar radiation and darkness with a mixture of carbon dioxide and air.

2. The method of claim 1 wherein said mixture of carbon dioxide and air in both stages contains 1–5% by volume of carbon dioxide.

3. The method of claim 1 wherein said mixture of carbon dioxide and air in both stages contains 5% by volume of carbon dioxide.

4. The method of claim 1 wherein said alga cells are cells of the alga *Porphyridium aerugineum.*

5. The method of claim 1 wherein the temperature of said aqueous culture is maintained during said diurnal cycles of solar radiation and darkness at a level conducive to the growth of said alga cells.

6. The method of claim 5 wherein said alga cells are cells of the alga *Porphyridium aerugineum* and said aqueous culture during said second stage is maintained at a temperature between 70° F. and 77° F. (21.1° C. and 25.0° C.).

7. The process of claim 1 wherein during said first stage the linear gradient of the cumulative absorbed radiant energy from the illumination versus time curve over the initial period of $0 < t < 2$ days, $\psi_a$, the cumulative absorbed moles of radiant energy quanta from the illumination, $(E_a)_c$, and lag time $\theta_l$ are manipulated.

8. The process of claim 7 wherein said alga is *Porphyridium aerugineum.*

9. The process of claim 8 wherein $\psi_a$ is about 0.33 Einstein (0.0165 kw-hr) per day, $(E_a)_c$ is between about 0.66 and 0.89 Einstein (0.033 and 0.045 kw-hr) per liter, and $\theta_l$ is about 40 hours.

10. The process of claim 7 wherein, in the first stage, the energy content of the artificial illumination is predominantly in the region of about 600 to 700 nanometers.

11. A method for the synthesis of biopolymer from the alga *Porphyridium aerugineum* comprising in a first stage contacting an aqueous culture containing cells of said alga and nutrients required for the growth of said alga cells with a mixture of carbon dioxide and air containing about 5% by volume of carbon dioxide and subjecting said aqueous culture to the action of artificial illumination of said intensity and for such time that synthesis of alga biopolymer begins and in a second stage subjecting said aqueous culture to diurnal cycles of solar radiation and darkness, contacting said aqueous culture continuously during said diurnal cycles of solar radiation and darkness with a mixture of carbon dioxide and air containing about 5% by volume of carbon dioxide, and maintaining the temperature of said aqueous culture during said diurnal cycles of solar radiation and darkness between 70° F. and 77° F. (21.1° C. and 25.0° C.).

12. A method for the synthesis of biopolymer from the alga *Porphyridium aerugineum* comprising in a first stage contacting an aqueous culture containing cells of said alga and nutrients required for the growth of said alga cells with a mixture of carbon dioxide and air containing about 5% by volume of carbon dioxide and subjecting said aqueous culture to the action of artificial illumination wherein the initial linear gradient of the cumulative absorbed radiant energy from the illumination versus time curve over the initial period of $0 < t < 2$ days, is about 0.33 Einstein (0.0165 kw-hr), the cumulative absorbed moles of radiant energy quanta from the illumination, is at least between 0.66 and 0.89 Einstein (0.033 and 0.045 kw-hr) per liter, and $\theta_i$ is about 40 hours and the energy content of the illumination is predominantly in the region of about 600 to 700 nanometers, and in a second stage subjecting said aqueous culture to diurnal cycles of solar radiation and darkness, contacting said aqueous culture continuously during said diurnal cycles of solar radiation and darkness with a mixture of carbon dioxide and air containing about 5% by volume of carbon dioxide, and maintaining the temperature of said aqueous culture during said diurnal cycles of solar radiation and darkness between about 70° F. and 77° F. (21.1° C. and 25.0° C.).

* * * * *